United States Patent [19]

Pfleger

[11] Patent Number: 4,929,230

[45] Date of Patent: May 29, 1990

[54] SYRINGE CONSTRUCTION

[76] Inventor: Frederick W. Pfleger, 1152 Barbara Dr., Cherry Hill, N.J. 08003

[21] Appl. No.: 252,792

[22] Filed: Sep. 30, 1988

[51] Int. Cl.$^5$ .............................................. A61M 5/22
[52] U.S. Cl. ..................................... 604/90; 604/191; 604/238
[58] Field of Search .................... 604/56, 82, 89, 90, 604/91, 191, 219, 232, 238, 236; 222/386; 206/219

[56] References Cited

U.S. PATENT DOCUMENTS

| | | | |
|---|---|---|---|
| 2,591,046 | 4/1952 | Brown | 604/90 |
| 2,708,438 | 5/1955 | Cohen | 604/192 |
| 3,075,525 | 1/1963 | McConnaughey | 604/89 |
| 3,091,240 | 5/1963 | McConnaughey et al. | 604/90 |
| 3,667,652 | 6/1972 | Morane et al. | 604/56 |
| 3,699,961 | 10/1972 | Szpur | 604/89 |
| 3,941,128 | 3/1976 | Baldwin | 604/238 |
| 3,976,069 | 8/1976 | Ong | 604/232 |
| 4,439,184 | 3/1984 | Wheeler | 604/191 |
| 4,529,403 | 7/1985 | Kamstra | 604/191 |
| 4,744,790 | 5/1988 | Jankowski et al. | 604/232 |

Primary Examiner—Stephen C. Pellegrino
Assistant Examiner—Ralph Lewis

[57] ABSTRACT

A syringe for hypodermic injection wherein multiple pistons seal various number of chambers. One piston provides the basic operating force to dispell the contents from a chamber or successive chambers and another piston or other pistons forming a chamber or additional chambers permitting release of the chamber contents or successive chamber contents and a syringe holder for holding, using and disposing of the syringe minimizing potential of accidental sticking by the needle of the syringe.

23 Claims, 3 Drawing Sheets

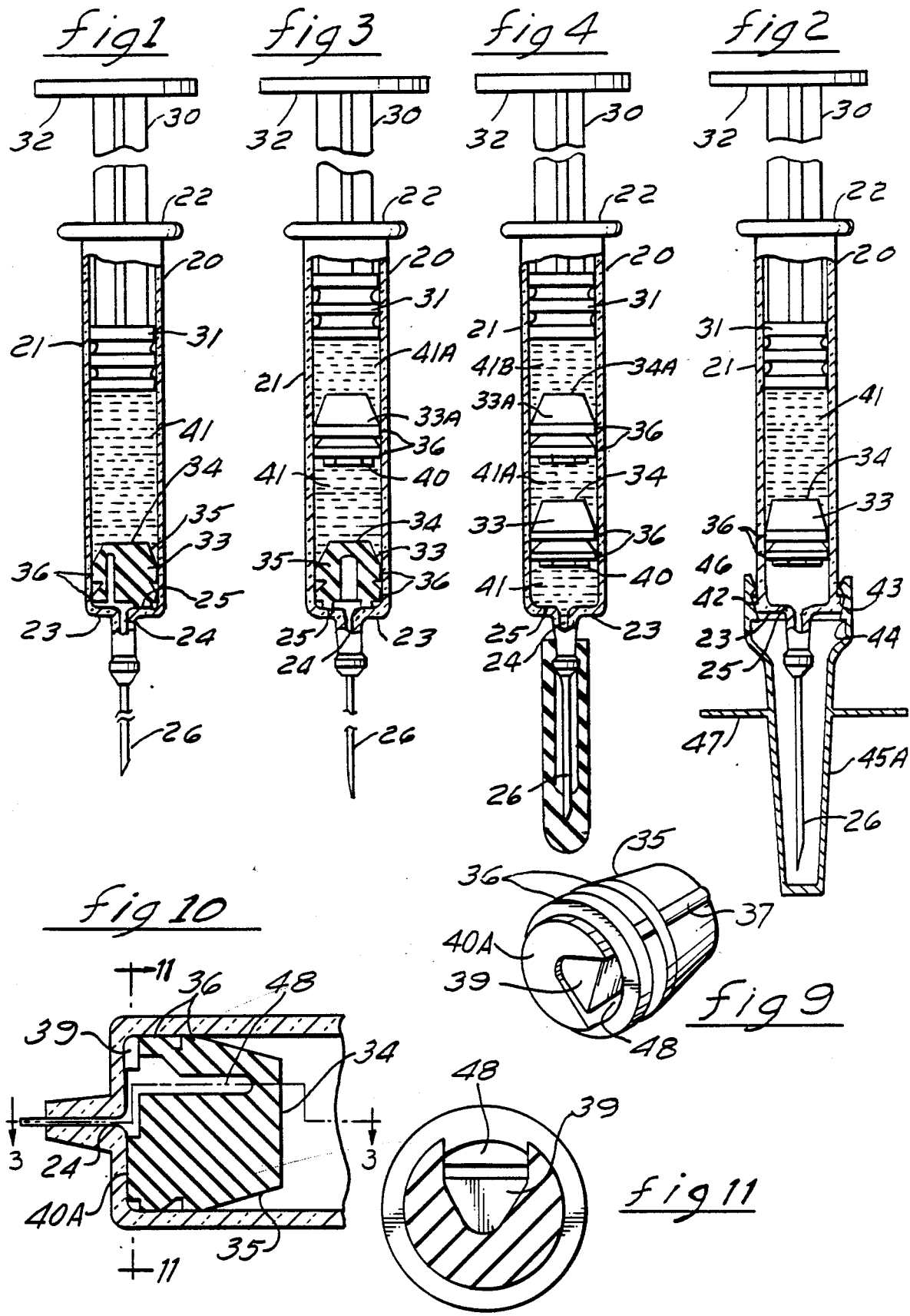

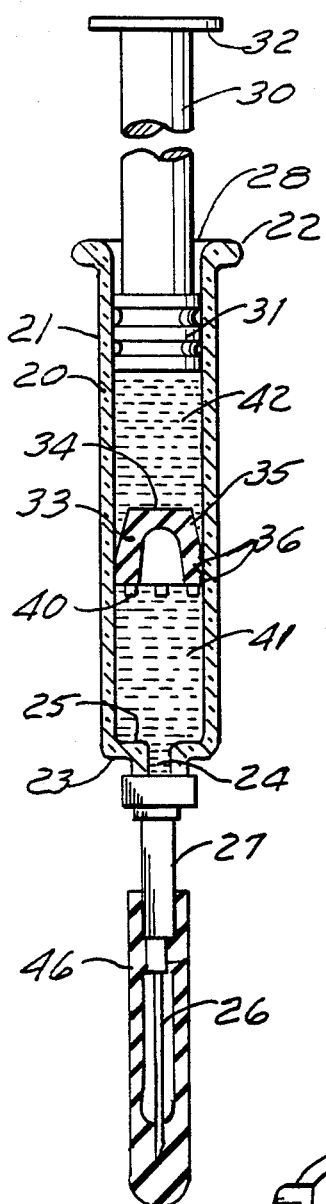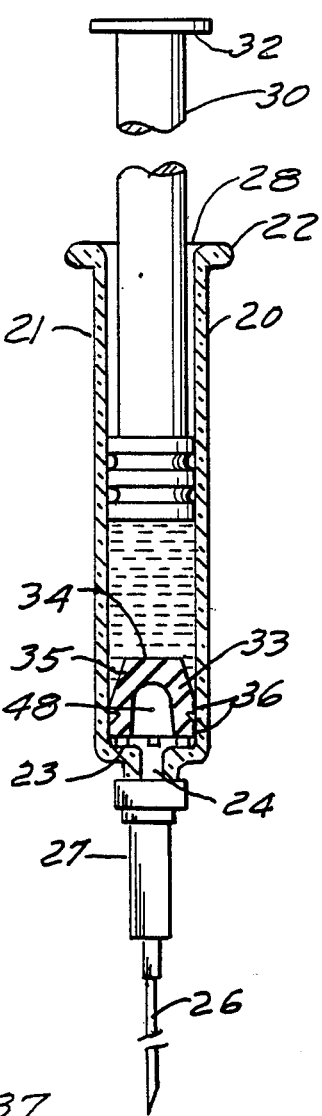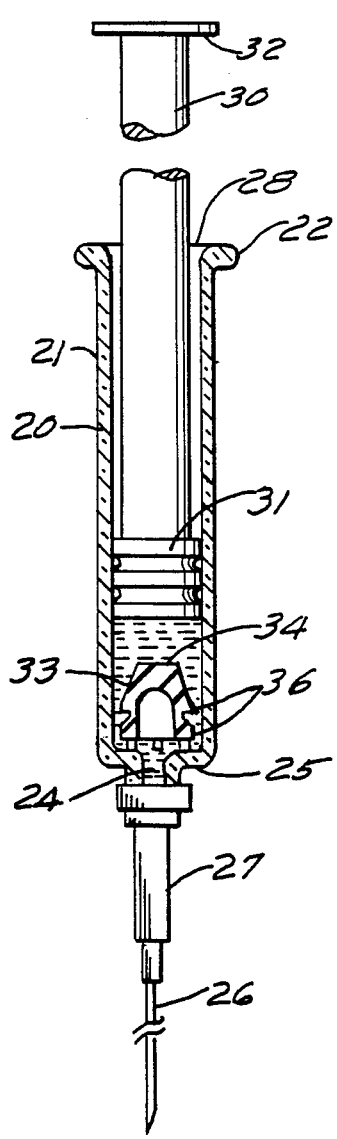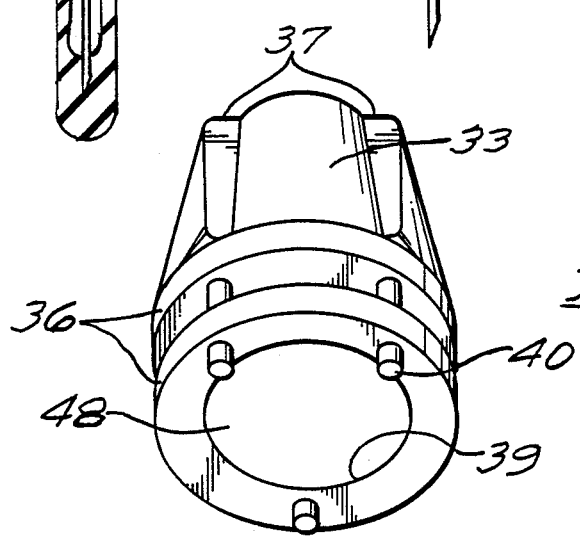

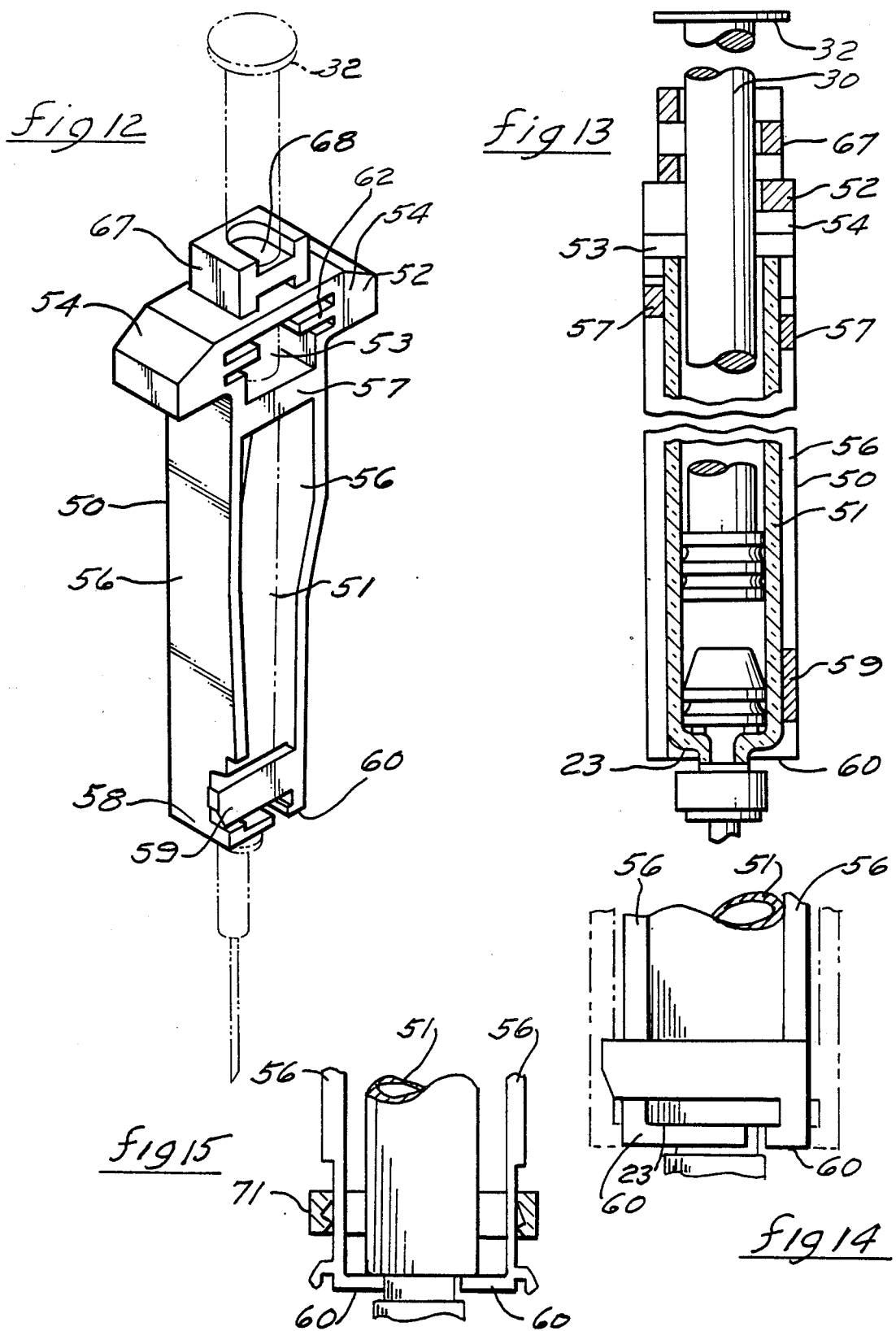

SYRINGE CONSTRUCTION

BACKGROUND OF THE INVENTION

As it is well known, the spread of infection by hypodermic needles is a serious problem, especially as one using a hypodermic injector is very likely to touch the needle and be infected by contact. It is also noted that the sequential injection of contents while maintaining the contents separate is a problem not heretofore satisfactorily overcome. It is also noted that the present art of syringes with sealed off compartments within the syringe require prior functions before it can be used.

Applicant is aware of the below listed prior patents:

| NAME | PATENT NO. | DATE |
| --- | --- | --- |
| FLETCHER | 1,867,355 | JULY 12, 1932 |
| WHITAKER ET AL | 2,720,880 | OCT. 18, 1955 |
| DEBAZ | 2,829,643 | APRIL 8, 1958 |
| McCONNAUGHEY ET AL | 3,091,240 | MAY 28, 1963 |
| STEVENS | 3,911,916 | OCT. 14, 1975 |
| ONG | 3,976,069 | AUG. 24, 1976 |
| BARTNER | 4,394,863 | JULY 26, 1983 |
| WHEELER | 4,439,184 | MARCH 27, 1984 |
| GAHWILER | 4,465,476 | AUG. 14, 1984 |
| KAMSTRA | 4,496,344 | JAN. 29, 1985 |
| MILLER ET AL | 4,540,405 | SEPT. 10, 1985 |
| BRUNET | 4,643,721 | FEB. 17, 1987 |

SUMMARY OF THE INVENTION

Among the objects of the present invention is to provide a hypodermic injector wherein contents in one or more separate chambers may be reliably injected sequentially from the separate chambers.

It is a more particular object of the present invention to provide a closed chamber within a syringe to store the contents free from contact with external objects such as the metal needle.

It is a more particular object of the present invention to provide a closed chamber within a syringe and still be able to inject from the syringe without requiring activation of the syringe by motions other than those used in injections.

It is a more particular object of the present invention to provide a syringe for sequential injection of two or more materials wherein an intermediate free piston or pistons are slidable in a syringe tube having a circumferential surface in sealing engagement about the interior surface of the syringe tube to separate the contents and being changeable under differential pressure to automatically pass the second or successive contents to be injected.

It is a more particular object of the present invention to provide a hypodermic injector for injecting one or more sequential contents with a syringe holder by which the syringe is retained, used and discarded with little chance of coming in contact with the needle.

It is another object of the present invention to provide a hypodermic syringe in which the contents are confined by elements within the syringe and a needle cover of ample size and material to prevent accidental puncturing of the administrator.

Other objects of the present invention will become apparent upon reading the following specification and referring to the accompanying drawings, which form a material part of this disclosure.

This invention accordingly consists in the features of construction, combinations of elements, and arrangements of parts, which will be exemplified in the construction hereinafter described, and of which the scope will be indicated by the appended claims.

BRIEF DESCRIPTION OF THE DRAWINGS

FIG. 1 is a longitudinal sectional view of a single chamber hypodermic ready for use.

FIG. 2 is a longitudinal sectional view of a single chamber hypodermic with the contents stored in an intermediate position in the syringe tube.

FIG. 3 is a longitudinal sectional view of a 2 chamber hypodermic ready for use taken along line 3—3 FIG. 10.

FIG. 4 is a longitudinal sectional view of a 3 chamber hypodermic ready for use.

FIG. 5 is a longitudinal sectional view of a 2 chamber hypodermic using a different configuration of chambers.

FIG. 6 is a view similar to FIG. 5 with the material in the one chamber discharged.

FIG. 7 is a view similar to FIG. 6 showing the contents of chamber 2 flowing past the free piston.

FIG. 8 is a perspective of one type of free piston.

FIG. 9 is a perspective of a second type of free piston.

FIG. 10 is a cross section of the second type of free piston.

FIG. 11 is a cross section generally along line 11—11 of FIG. 10.

FIG. 12 is a perspective of a holder for holding the syringe if the syringe is made without a finger flare.

FIG. 13 is a cross section generally along line 13—13 of FIG. 12.

FIG. 14 is a partial view showing the holder in open and closed position.

FIG. 15 is a partial view similar to FIG. 14 with a separate clip member for transferring the holder from its open position to its closed position.

DESCRIPTION OF THE PREFERRED EMBODIMENTS

Referring now more particularly to the drawings, and specifically to FIGS. 1-7, there is shown a hypodermic needle or syringe, generally designated 20 and including a generally cylindrical tube or cartridge 21, ordinarily of glass or plastic. The tube 21 has an open end 28, the upper end in FIGS. 1-7, open as by an outturned lip or flange 22. The other, lower end of the cylindrical tube 21 is reduced, as by an end wall or shoulder 23 to a reduced outlet port 24. Thus, the interior of the reducing end wall 23 may provide an annular internal shoulder, as at 25.

Extending from the reduced outlet port 24 may be an injection needle 26 communicating with the interior of the tube 21 through a connector 27 or secured to the inside of nipple 24.

On a rod 30 extending into the open end 28 of the tube or cylinder 21 is a piston 31 in snug sliding engagement with the interior of the tube. The piston or enlarged head 31 on the rod 30 may be of rubber or other suitable sealing material, and the rod 30 may be provided on its outer end, exteriorly of the tube 21 with a head 32.

Interiorly of the tube 21, between the piston 31 and the shoulder 25, there is a free piston 33 also in snug sliding engagement with the interior of tube 21.

The free piston 33 may be of a flexible rubber like material and of a hollowed shaped configuration 48 facing toward the end wall 23. This hollowed shape 48 may be circular in shape as shown in FIGS. 5, 6, and 7 or it may be flat and narrow in shape as shown in FIGS. 9, 10 and 11. It may also be filled with a low strength compressible resilient material. More specifically, the free piston 33 includes a closed end 34 of less external diameter than the interior of the tube 21, and a peripheral side wall 35 extending from the closed end 34 obliquely outwardly to the interior of the tube 21. The oblique side wall 35 terminates at its larger end in a generally cylindrical peripheral sealing surface 36 in slideable conforming engagement with the interior of the cylindrical wall of tube 21. Further, free piston 33 has its large end of side wall 35 generally cylindrical, as sealing surface 36, for sealing engagement with the interior of tube 21. As shown in FIGS. 1-4, this sealing surface 36 may be two or more surfaces. The free piston side wall 35 may have external ribs 37 extending generally from the sealing surface 36 to the closed end 34 of the free piston 33. These ribs help to prevent tipping of the piston as it moves in the tube 21. Thus, the free piston 33 is generally hollow, with a generally flat closed end 34, and a flaring side wall 35 terminating in a sealing surface 36.

The hollow end 48 is provided with a plurality of lugs 40 as shown in FIG. 4 or a stopper movement inhibitor surface 40A 40A as shown in FIGS. 9 and 10. A path 39 for the contents of the syringe to flow through is generated by the lugs 40 or by the opening in the annular ring 40A. Stopper movement inhibitor surface array of lugs 40 or the stopper movement inhibitor surface 40A is engagable with the internal shoulder 25, the condition shown in FIGS. 1, 6, and 10.

As shown in FIGS. 1-4, the free piston 33 can be located in the syringe 20 in different positions to allow different uses of the syringe. FIG. 1 shows the free piston 33 located adjacent to internal shoulder 25. In this position the syringe has only 1 contents chamber 41. FIG. 2 also shows a one contents chamber 41 with the contents stored in the tube 20 still sealed by the inner wall of the tube 21, the piston 31, and the free piston 33. As shown in FIG. 3, two free pistons 33 are used in the syringe 20. The lower free piston 33 located adjacent the internal shoulder 25, the intermediate piston 33A, and the inner wall of tube 21, form the first contents chamber. The intermediate piston 33A, piston 31, and the inner wall of tube 21 forms a second contents chamber. As shown in FIG. 4, three (3) content chambers are shown. The lower or first content chamber is composed of the free piston 33, the needle seal 45, and the inner wall of tube 21. Chamber 2 comprises 2 free pistons 33 and 33A, and chamber 3 comprises a free piston 33A and piston 31. It is possible to add additional chambers therefore merely by adding additional free pistons 33. If a free piston were used as shown in FIG. 1 adjacent surface 25 in the syringe shown in FIG. 4, the lower chamber would be made up of two free pistons 33 and the inner wall of tube 21. In this arrangement the needle seal 45 would not be needed. FIG. 5 shows a two chamber syringe in which a needle seal 45 forms a part of the lower chamber.

As a result it has been shown that a free piston 33 can be used to provide a syringe with 1, 2, 3 or more content chambers.

In order to discharge the contents from the syringe, the needle seal 45 must be removed from the syringe filled with content as shown in FIGS. 4 and 5. If the syringes are filled as shown in FIGS. 1, 2, 3 it would only be necessary to remove a cover 45A similar to that shown in FIG. 2 if the syringe is a sterile application. If the syringe is not a sterile type application, no cover would be needed on the syringe output port since the contents are sealed inside the syringe.

Since accidental puncturing of the administrator of the contents of the syringe is becoming more serious, as an example, administering a medicine to a patient with a serious or contageous disease, a needle cover 45A which helps prevent this accidental puncture is shown in FIG. 2. As previously described, the contents to be injected is contained in the chamber inside the syringe. As a result the needle cover 45A does not have to seal the syringe, but has to keep the needle clean and sterile. This can be accomplished by a cover which employs the principle of "tortous path;" that is, there cannot be a straight path to the item to remain sterilized. As a result tube 21 is provided with a lip 42 with a locking corner 43. The cover 40 is provided with a mating locking corner 44 as well as tapered assembly surface 46. In storage, or prior to use, the cover 40 is assembled to the tube 21 with the tapered assembly surface 45 engaging the lip 42, thus retaining it in position. In using the syringe, the administrator removes the cover 45A by sliding it off the lip 42. The cover 45A is designed to have enough yield at this point to allow for the circumferential stretch. After the needle is used, the needle can be very contageous. As a result the cover 45A or seal 45 must be replaced. As can be seen in FIGS. 2 and 4, the target area to reinsert the needle 26 is much larger in FIG. 2 than in FIGS. 4 and 5. Since the seal 45 shown in FIG. 4 also must be sealable against the needle 26, the material normally used for this function is a rubber or rubber like material. As a result it is possible for the needle even though it has entered the target hole to pierce the material of the seal and puncture the administrator. Besides having a larger target, the cover 45A shown in FIG. 2 can be made of a solid plastic material which cannot be punctured by the needle. In order to prevent the needle from ever becoming reexposed, the cover is reinserted onto tube 21, a greater distance than from which it was removed. Moving this further distance engages locking corner 44 of the cover with locking 43 of the tube 21 thus locking the cover to the tube. An additional flange or shield 47 can be added to cover 45a for further protection as well as aid in reassembly of the cover.

After the needle 45 has been removed, pressure applied to head 32 is transmitted to piston 31 and then onto the contents of the chamber adjacent piston 31. If the syringe contents are filled as shown in FIG. 2, this pressure will move the contents and the free piston toward the outlet 24 until the movement inhibitor surface 40a of free piston 33 comes into contact with internal shoulder 25. If the syringe contents are filled as shown in FIGS. 4 and 5 moving of free piston towards the outlet 24 will push the contents 41 to the outlet.

Although the free piston 33 is in sealing engagement with the inside of tube 21, due to the resilience of the material of free piston 33 and the interference fit between them, pressure on piston 31, onto contents 41A could have a tendency to push the contents past the seal and mix it with the contents in chamber 41. In order to prevent this, movement of free piston 33 builds up pressure in chamber 41 since the area of the discharge port and the needle 26 is much less than the area of the inside of tube 21. This build up of pressure, causes the free piston 33 to move which not only forces the fluid through the needle 26, but the reactive force of the contents in chamber 41 applies equal and opposite forces to the internal surface 48a of hollow shape 48 of free piston 33. Since fluids under pressure produce equal forces in all directions, the contouring of the internal surface 48 produces additional radial forces to side wall 35 and sealing surface or surfaces 36.

As a result the more force applied to the head 32, the higher the sealing force if there is contents in the adjacent chamber, thus preventing the passage of the contents of chamber 41 entering chamber 41A or the contents of chamber 41A entering chamber 41 when contents are in chamber 41. When the contents in chamber 41 is exhausted, no further additional sealing forces are generated.

When no further additional sealing forces exist, the sealing force still generated by the resilence of the material and the interference fit still exists. In order to allow the contents of the next chamber to flow to the outlet port 24; the free piston 33 is provided with a method for the content to bypass the free piston when the free piston 33 has engaged internal shoulder 25.

The forces generated on the contents by piston 31 when the pressure is applied to head 32 will move the free piston or pistons 21 axially in the tube 33. When the free piston 33 is against the end surface 25, the forces on the contents on the side wall 35 will overcome the resilient material sealing forces of free piston 33. Over coming the resilient material sealing force will cause the side wall 35 to collapse inwardly, since the resilient material sealing forces are lower than the forces related to those provided by piston 31. The circumferential position of the collapsing of the wall 35 of free piston 33 will be indeterminate on free piston designs shown in FIG. 8. In FIGS. 9-10 and 11 and 12, the circumferential position is controlled by the thin wall location in the design. The thinner the wall the weaker the resilient sealing force: as a result the force at which the wall will collapse or move inwardly is controlled by the design of the wall.

As shown in FIG. 7, when wall 35 collapses, the contents moves past the wall 35 and into the spaces generated by lugs 40. In FIG. 11 collapse of the thinner wall 35 will allow the contents to flow past the free piston 33 and into the path 39 to the output port 14 and needle 26.

Thus in preparation for the dispensation of contents, from a syringe as shown in FIG. 5, a first content is introduced, as at 41, into the tube 21, being located between the tube end 23 and the free piston 33. A second content 41a is contained in the space between the free piston 33 and the piston 31. As the sealing surface 36 of the free piston 33 engages about its periphery in sealing engagement with the interior of the tube 21, the contents 41 and 41a are normally maintained separate and apart.

Movement of plunger 31 into the cylinder 21 displaces the fluid 41 out of the cylinder and moves the free piston 33 to a position with the lugs 40 movement inhibitor surface 40a just engaging the surface 25 of the tube end wall 23.

Continued movement of the plunger 31, and thus the fluid 41a will create the pressure differential on opposite sides of the free piston 33. As the pressure of fluid 41a is increased on the wall 35 of the free piston 33, the wall 35 will be displaced inwardly, as in FIG. 7, to pass fluid 41a around the plunger 33 and through the interlug spaces 45, as seen in the condition of FIG. 7 for ejection through needle 26.

In preparation for the dispensation of contents from a syringe as shown in FIG. 1, a content to be injected is introduced as at 41. Movement of piston 31 inwardly into the tube seats the movement inhibitor surface 40a of the free piston 33 adjacent the surface 25 of tube end 23. Further inward movement of piston 31 causes the flow of the contents past the free piston 33 similarly described above.

In preparation for dispensation of contents from a syringe as in FIG. 4, contents are introduced as at 41, 41A and 41B. Movement of piston 31 inwardly into the tube ejects the contents of chamber 41 until movement inhibitor surface 40a free piston 33 is adjacent the surface 25 of tube end 23. Further movement of piston 31 into the chamber moves the contents of chambers 41A past the free piston 33 by the movement of free piston 33A moving the contents out of chamber 41A until the movement inhibitor surface 40a free piston 33A is adjacent the closed end 34 of free piston 33. Still further movement of piston 31 moves the contents from chamber 41B past the collapsed free piston 33A and collapsed free piston 33 to the outlet port 24 in surface 25.

FIGS. 12-13 illustrate a holder constructed in accordance with instant invention. A holder is generally designated 50, as in FIGS. 12 and 13, serves to hold a hypodermic syringe cartridge 51. The hypodermic syringe cartridge 51 is basically the same as the syringe 20 shown in FIGS. 1-7 except that the flange 22 is eliminated. The hypodermic syringe cartridge 51 is shown in longitudinal section in FIG. 13, and in phantom in FIG. 12. The holder 50 may be molded of plastic, or otherwise suitably formed, and includes a transversely enlarged upper end portion or head 52 having a central opening 53 from which extend laterally outwardly a pair of finger holds 54.

Depending from respective finger holds 54, spaced inwardly from the ends thereof, are a pair of side members 56 which converge in the downward direction away from the enlarged head 52. The elongated side members 56 extend longitudinally of each other away from the enlargement or head 52. A pair of cross-pieces or transverse members 57 extends between the elongated side members 56 in the region adjacent to the head 52. Thus, the elongated members 56 are free to swing toward and away from each other from the cross-pieces 57 to their free ends 58. Advantageously a snap hook 59 is provided adjacent to one end of one elongated side member 56 for a selective holding engagement with the other side member 56. Upon opening of the snap hook 59, the elongated side members 56 spread apart for receiving there between the tube 51 of an ejection device.

Further, the tube 51 of the ejection device has its forward end 23 in bearing engagement with inturned ends 60, FIGS. 13 and 14 on the lower ends elongated side members 56. That is, the inturned elements 60 on the ends of the elongated side members 56, serve to retain the tube 51 in position within the carrier or holder 50.

More specifically, entering from opposite finger holds 54 of the head 52 partially into the space 53 are a pair of resilient fingers 62. That is, the resilient fingers 62 extend inwardly from opposite side members 54 into the space 53, there terminating short of each other for resilient bearing engagement of the members with the end of tube 51 to position the latter longitudinally in the holder 50.

As a result, the tube 51 is held longitudinally between the inturned ends 60 and the resilient fingers 62, while the tube is held laterally with its upper region engaging crossmembers 57 and its lower region held by the elongated side members 56 removeably secured by the snap clip 59.

The lower ends of elongated side members 56 of holder 50 are releaseably retained snugly against the tube 51, with the inturned ends 60 engaging about the end 23 of the tube 51, FIGS. 13 and 14. The latch 59 may be opened to release the elongated side members 56, FIG. 14 for movement away from the tube 51, whereby the tube is released for outward swinging movement beyond inturned ends 60 and dropped from the holder 50.

A guide member 67 on the upper end of head 52, is provided with a through hole 68 for guiding and retaining rod 30.

Thus, an ejector without the flange 22, may be carried by a holder 50 in the manner described above, and a rod 30 with a head 32 applied thereto.

FIG. 15 illustrates a slightly modified embodiment wherein elongated side members 56 have a portion of the leg adjacent the inturned ends 60 modified to retain a clip 71 slideable to shift the inturned ends 60 to the holding position with respect to the tube 51 as shown by the solid lines.

From the foregoing, it is seen that the present invention provides a syringe for hypodermic injection of contents from a single closed chamber closed by several methods, of sequential contents from separate closed chambers and a holder for the injection device, if desired, all of which are extremely simple in construction and accomplish their intended objects without departing from the spirit of the present invention.

What is claimed is:

1. A hypodermic syringe comprising; a cylindrical tube, an outlet port at one end of said tube, a resilient material pressurizing piston extending inwardly from the other end of said tube, a resilient material free piston located between said pressurizing piston and said outlet port, said pressurizing piston said free piston and said cylindrical tube forming a chamber, said chamber capable of holding contents, an external sealing surface on a first end of said free piston, said first end located closest to said outlet port, a smaller second end of said free piston, said second end closest to said pressurizing piston, a tapered surface between said sealing surface and said smaller second end of said free piston, a civity of greater depth than the longitudinal length of said external sealing surface of said free piston, a wall between said tapered surface and said cavity, wherein said wall is collapsible into said cavity when pressure on said tapered wall exceeds the pressure of said sealing surface.

2. A hypodermic syringe according to claim 1 including a second free piston located between said first free piston and said pressurizing piston dividing said chamber into a first portion and a second portion, each of said portions capable of holding contents.

3. A hypodermic syringe according to claim 1 including a seal means on said outlet port, said free piston and said seal means forming a second chamber, said second chamber capable of holding a contents.

4. A hypodermic syringe according to claim 3 wherein pressure on contents in said second chamber causes an increase in the pressure of said external seal surface of said free piston.

5. A hypodermic syringe according to claim 4 including a seal means on said injection needle, said free piston said seal means on said needle and said cylinder forming a second chamber, said second chamber capable of holding contents.

6. A hypodermic syringe according to claim 1 including a compressible material in said cavity said compressible material capable of compressing by movement of said collapsible wall.

7. A hypodermic syringe according to claim 1 including a hollow needle attached to said outlet port.

8. A hypodermic syringe according to claim 7 including a corner on said cylindrical tube proximate to said outlet port, a cover for said needle, a tapered surface on the inside of said cover, a locking corner on the inside of said cover, said corner on said cylindrical tube engaging said tapered surface for storage and said corner of said cylindrical tube engaging said locking corner on said cover after reapplying said cover to said cylindrical tube.

9. A hypodermic syringe according to claim 1 including a multiplicity of free pistons located between said free piston and said pressurizing piston dividing said chamber into a multiplicity of chambers each chamber capable of holding contents.

10. A hypodermic syringe according to claim 1 including stabilizing surface on said free piston, said stabilizing surface acting with said cylindrical tube to maintain alignment in said cylindrical tube.

11. A hypodermic syringe according to claim 1 in combination with guide ribs on the exterior of said free piston for guiding engagement with said tube to maintain the free piston and tube in said sealing relation.

12. A hypodermic syringe according to claim 1, in combination with a holder comprising a head piece in bearing engagement with the other end of said tube, a pair of side members extending from said head piece on opposite sides of said tube and resiliently flexible toward and away from each other and said tube, and interfitting formations on said side members releasably retaining the latter toward each other for releasably holding said tube in said holder.

13. A hypodermic syringe according to claim 12, in combination with retainers on said side members located for retaining said tube in said holder when the side members are toward each other, said retainers being spaced apart on spreading of said side members for releasing the tube from the holder.

14. A hypodermic syringe according to claim 12, said holder head piece comprising at least one spring finger in bearing engagement with said other tube end for retaining the tube in position toward a retainer, said spring finger extending transversely of said holder for resilient deflection on engagement with said other tube end.

15. A chamber comprising; a pressurizing portion, a discharge end, a resilient material plug located proximate to said discharge end, means to restrict movement of said resilient material plug, a first end and a second end on said resilient material plug, said first end facing said discharge end of said chamber and said second end facing said pressurizing portion of said chamber an annular surface of seal assuring capability proximate to said first end of said plug, a sealing condition between said annular surface and said chamber, a tapered wall extending from said annular closest to said outlet port, a smaller second end of said free piston, said second end closest to said pressurizing piston, a tapered surface between said sealing surface and said smaller second end of said free piston, a cavity of greater depth than the longitudinal length of said external sealing surface of said free piston, a wall between said tapered surface and said cavity, wherein said wall is collapsible into said cavity when pressure on said tapered wall exceeds the pressure of said sealing surface.

16. A chamber according to claim 15 including a second resilient material plug located between said first resilient material plug and said liquid pressurizing portion, said chamber formed into a first content chamber between said first and second resilient material plugs, a second contents chamber between said second resilient material plug and said pressurizing section, said first plug collapsible by pressure from said first contents and said second plug collapsible from pressure from contents in said second chamber when said second resilient material plug is restricted from movement by said first resilient material plug.

17. A chamber according to claim 15 including a seal means for said discharge end, said chamber comprising a first content chamber between said seal means for said discharge end and said first end of said resilient material plug and a second contents chamber between said second end of said resilient material plug and said pressurizing portion.

18. A moveable resilient material separator according to claim 17 including a compressible material in said cavity, said compressible material compressible by the collapse of said collapsible connecting wall.

19. A chamber according to claim 15 including a multiplicity of resilient material plugs, said chamber comprising a multiplicity of sections each section located between a said second end of a plug and said first end of the following plug.

20. A chamber according to claim 15 including a seal means for said discharge end, a multiplicity of resilient material plugs, said chamber comprising a multiplicity of successive sections, said seal and said first end of the first of said plugs forming said first section and said second end of said plugs and said first end of said successive plugs forming the successive sections.

21. A moveable resilient material separator for each section of a multi-section pressurizible chamber comprising a first end on said separator, an annular surface positioned relative to said first end of said separator for sealing between each section of said chamber, a second end of said separator, said second end of said separator being of a smaller dimension than said annular surface, a cavity extending into said separator from said first end, a collapsible connecting wall between said annular surface and the bottom of said cavity, an outer surface on said wall, an inner surface on said wall, said collapsible connecting wall collapsible into said cavity by pressure from said pressurizable means when said separator is restricted from movement.

22. A moveable resilient material separator according to claim 21, including means to restrict separator movement comprising a stop surface proximate to said first end of said separator to restrict movement when acting with a stop on said chamber.

23. A moveable resilient material separator according to claim 22 wherein said first end of the separator may contact said second end of a proceeding separator to restrict movement of succeeding separators.

* * * * *